(12) United States Patent
Gertz et al.

(10) Patent No.: US 10,247,679 B2
(45) Date of Patent: Apr. 2, 2019

(54) CALIBRATION AND DETECTION OF SILICONE OIL IN SYRINGE BARRELS

(71) Applicant: ZebraSci, Inc., Temecula, CA (US)

(72) Inventors: Frederick Talley Gertz, Riverside, CA (US); Robert James Schultheis, Temecula, CA (US); Jaan Noolandi, La Jolla, CA (US)

(73) Assignee: ZebraSci, Inc, Temecula, CA (US)

( * ) Notice: Subject to any disclaimer, the term of this patent is extended or adjusted under 35 U.S.C. 154(b) by 38 days.

(21) Appl. No.: 15/293,573

(22) Filed: Oct. 14, 2016

(65) Prior Publication Data

US 2017/0108451 A1 Apr. 20, 2017

Related U.S. Application Data

(60) Provisional application No. 62/242,346, filed on Oct. 16, 2015, provisional application No. 62/259,175, filed on Nov. 24, 2015.

(51) Int. Cl.
| | | |
|---|---|---|
| *G01N 21/95* | (2006.01) | |
| *G01N 21/954* | (2006.01) | |
| *A61L 31/10* | (2006.01) | |
| *A61L 31/14* | (2006.01) | |
| *A61M 5/31* | (2006.01) | |
| *G01N 21/64* | (2006.01) | |
| *G06T 7/00* | (2017.01) | |
| *G01N 21/90* | (2006.01) | |
| *G01N 21/93* | (2006.01) | |
| *G01N 21/88* | (2006.01) | |

(52) U.S. Cl.
CPC ............ *G01N 21/954* (2013.01); *A61L 31/10* (2013.01); *A61L 31/14* (2013.01); *A61M 5/3129* (2013.01); *G01N 21/643* (2013.01); *G01N 21/9018* (2013.01); *G01N 21/93* (2013.01); *G06T 7/0012* (2013.01); *A61L 2300/606* (2013.01); *A61L 2300/802* (2013.01); *A61L 2400/10* (2013.01); *A61L 2420/00* (2013.01); *A61L 2420/06* (2013.01); *A61M 2005/3131* (2013.01); *A61M 2205/70* (2013.01); *G01N 21/8851* (2013.01)

(58) Field of Classification Search
CPC ............... G01N 21/954; G01N 21/643; G01N 21/8851; G01N 21/9018; G01N 21/93; A61L 31/10; A61L 31/14; A61L 2300/606; A61L 2300/802; A61L 2400/10; A61L 2420/00; A61L 2420/06; A61M 5/3129; A61M 2005/3131; A61M 2205/70; G06T 7/0012
See application file for complete search history.

(56) References Cited

U.S. PATENT DOCUMENTS 5,991,018 A * 11/1999 Imaizumi ........... G01B 11/0616
356/237.1
6,239,870 B1 * 5/2001 Heuft .................... G01N 21/90
250/223 B (Continued)

*Primary Examiner* — Manav Seth
(74) *Attorney, Agent, or Firm* — Lumen Patent Firm

(57) ABSTRACT

Medical syringe barrels having the inner surface coated with cured silicone oil are used for calibration and detection of silicone oil in medical syringe barrels. Calibration standards as provided in this invention allow for quick determination how well a lubrication system for lubricating medical syringe barrels with silicone oil is working.

11 Claims, 12 Drawing Sheets

(56) References Cited

U.S. PATENT DOCUMENTS

| | | | | |
|---|---|---|---|---|
| 7,469,585 B2* | 12/2008 | Meyer | ............... | G01V 7/00 |
| | | | | 73/382 G |
| 7,648,487 B2* | 1/2010 | Ito | ............... | A61M 5/3129 |
| | | | | 604/230 |
| 8,512,796 B2* | 8/2013 | Felts | ............... | C23C 16/045 |
| | | | | 427/2.3 |
| 9,664,626 B2* | 5/2017 | Fisk | ............... | G01N 21/9072 |
| 9,930,297 B2* | 3/2018 | Alexander | ............... | H04N 7/185 |
| 2007/0270743 A1* | 11/2007 | Ackerman | ............... | A61M 5/3243 |
| | | | | 604/110 |
| 2009/0154789 A1* | 6/2009 | Wolfe | ............... | G01N 21/958 |
| | | | | 382/141 |

\* cited by examiner

Before Filling

After 2 Fillings

Sample: AM-001
Description: Sylgard 184 0.2µl spray, stored at room temperature
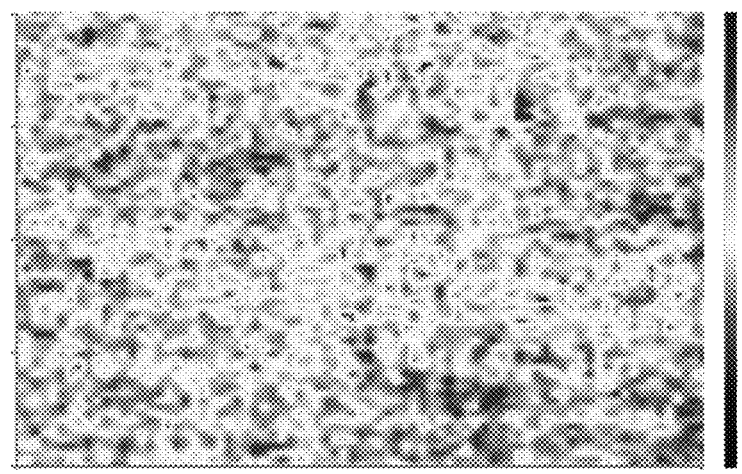
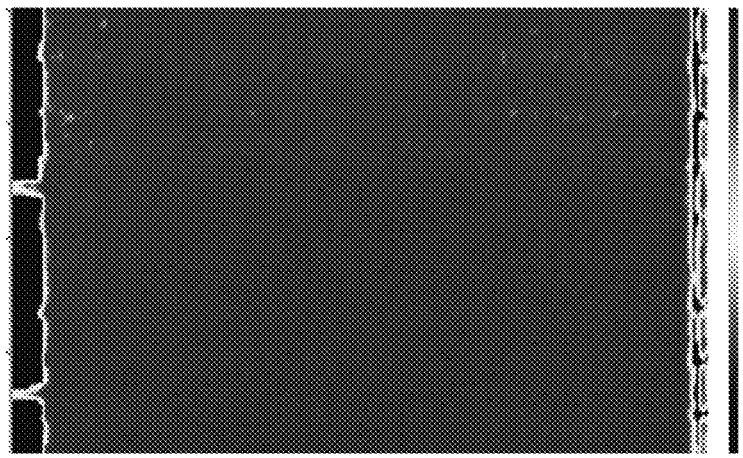
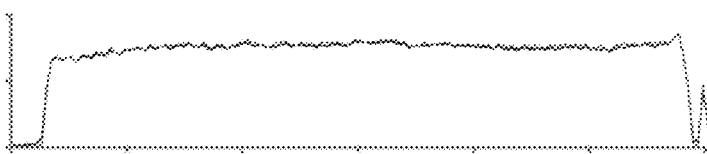
FIG. 8

Sample: AM-014
Description: Sylgard 184 0.2μl spray, immediately placed in furnace at 120°C and allowed to cure in furnace for at least one hour and then stored at room temperature.

Sample: AM-022
Description: Sylgard 184 0.2µl spray, filled with cell grade water and immediately placed in cold store after spray.
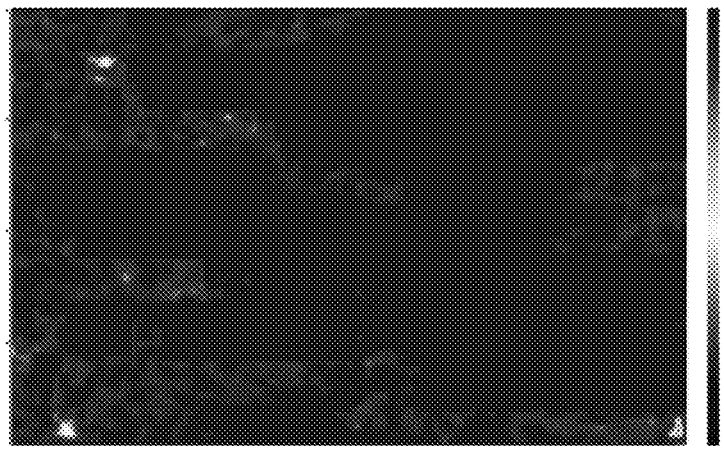
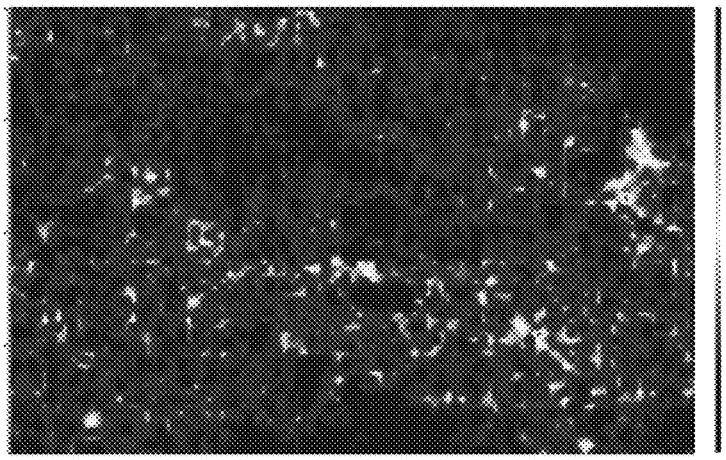
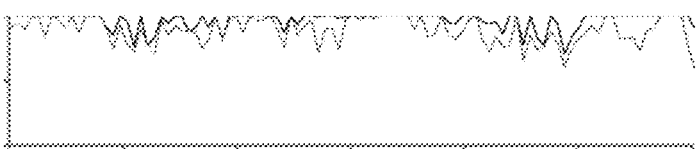
FIG. 10

Sample: AM-025
Description: Sylgard 184 0.2µl spray, filled with cell grade water and immediately placed in cold store after spray.

Sample: AM-031
Description: Sylgard 184 0.2μl spray, filled with cell grade water and immediately placed in cold store after spray.

CALIBRATION AND DETECTION OF SILICONE OIL IN SYRINGE BARRELS

CROSS-REFERENCE TO RELATED APPLICATIONS

This application claims priority from U.S. Provisional Patent Applications 62/242,346 filed Oct. 16, 2015 and 62/259,175 filed Nov. 24, 2015, which are incorporated herein by reference.

FIELD OF THE INVENTION

The invention relates to methods, systems and devices for calibration and detection of silicone oil in syringe barrels.

BACKGROUND OF THE INVENTION

PDMS Silicone oil (Polydimethylsiloxane) is a clear liquid, with a refractive index (~1.4) close to that of glass. As a lubricant it is particularly valuable in the pharmaceutical vial and syringe industry where it is recognized for its superior tribological properties, its optical transparency and its chemical and biological compatibility.

However the properties that make silicone oil popular also make it difficult to detect. Methods have been proposed for the detection and distribution of silicone oil in situ in drug vials, but these have shortcomings, one of which is the lack of high quality samples to calibrate the machines used for the detection and quantification of silicone oil. In this invention we advance the art by providing the use of a sample that utilizes a modified silicone oil, which can be cured on the surface of glass and chemically doped for enhanced detection.

SUMMARY OF THE INVENTION

The present invention provides a method and system for calibrating and detecting silicone oil in medical syringe barrels. A syringe barrel is provided which has the inner surface coated with silicone oil. An imaging system obtains or provides an image of the inner surface of the syringe barrel that has been coated with the silicone oil. Any type of imaging system can be used as long as it is capable of imaging/detecting silicone oil. A computer image analysis program executed by a computer is used to determine or calculate a distribution pattern of the silicone oil at the inner surface from the obtained image.

The computer image analysis program executed by the computer is further able to calculate a comparison between
(i) a distribution pattern of the silicone oil at the inner surface of the syringe barrel, and
(ii) a calibration distribution pattern of an inner surface of a calibration syringe barrel coated with a cured silicone oil.

An example of cured silicone oil is a curable Polydimethyisiloxane (PDMS). In any case, the silicone oil in the cured silicone oil is the same silicone oil as in the syringe barrel. The calibration distribution pattern of the cured silicone oil is obtained from a calibration image obtained with the same imaging system of the inner surface of calibration syringe barrel.

The computer image analysis program executed by the computer is then capable of outputting the comparison between both images. Heatmaps could be determined by the computer image analysis program and used for the comparison.

To enhance the imaging process the cured silicone oil could be chemically doped with a fluorescent material or a fluorescent tag that can be dissolved in silicone oil. In another example, the imaging process could be enhanced whereby the cured silicone oil is chemically or physically doped with a hydrophobic quantum dot. They are physically doped when they are mixed into the oil physically, but chemically doped when the surface of the quantum dots is modified by a hydrophobic material, otherwise they would phase separate from the oil after mixing.

In another embodiment the invention is a calibration syringe barrel whereby the inner surface of the syringe barrel is coated with cured silicone oil. The cured silicone oil defines a reference silicone oil distribution pattern, and the reference silicone oil distribution pattern is useful as a reference pattern for a silicone oil distribution pattern of other syringe barrels, which have the inner surface coated with silicone oil. The silicone oil in the cured silicone oil is the same silicone oil as in the other syringe barrels.

Embodiments of the invention allow for the creation of calibration samples for any type of pharmaceutical container chosen by a client. This allows the samples not only to be used for calibration when setting up/testing machines, but also to be used for daily checks in industrial settings, such as required by the stringent process controls currently in place in the pharmaceutical industry.

BRIEF DESCRIPTION OF THE DRAWINGS

FIG. 2A shows before filling and FIG. 2B shows after filling.

FIG. 5B shows an image with an uneven dispersion of Nile red fluorescent tag distributed throughout a layer of silicone oil. The filter used for this image is the standard TRITC DSU filter.

FIG. 7A shows an image with an uneven dispersion of Quantum dot fluorescent tag distributed throughout a layer of silicone oil. The white dots in the image show the position of the quantum dots. The filter used for this image is the standard TRITC DSU filter. FIG. 7B shows an image with a dispersions of Quantum dot fluorescent tag distributed throughout a layer of silicone oil using the same filter as the image in FIG. 7A. The edges of the oil layer contain higher concentrations of the tag and therefore show a brighter coverage.

FIGS. 8-12 show heat maps of six different samples according to an exemplary embodiment of the invention a top panel and a bottom panel, whereby the lower panel is the upper panel one month later after complete curing. The difference in samples is indicated by the description in each figure. As an example, FIG. 8 with sample AM-001 shows an excellent spray pattern both immediately after spraying and after one month. If the customers spray pattern looks like that of sample AM-001 in FIG. 8, their system is working perfectly. On the other hand if the customers spray pattern looks like that of sample AM-025 as shown in FIG. 11, there is clearly a problem with the uneven distribution of oil, and the customers system has to be recalibrated. The top panel and second panel from the bottom all have a y-axis ranging from 0 to 360 degrees. The second panel from the top and the bottom panel all have a y-axis ranging from 0 to 30 k micrometers square. All x-axis are in millimeters.

DETAILED DESCRIPTION

Figure 1:
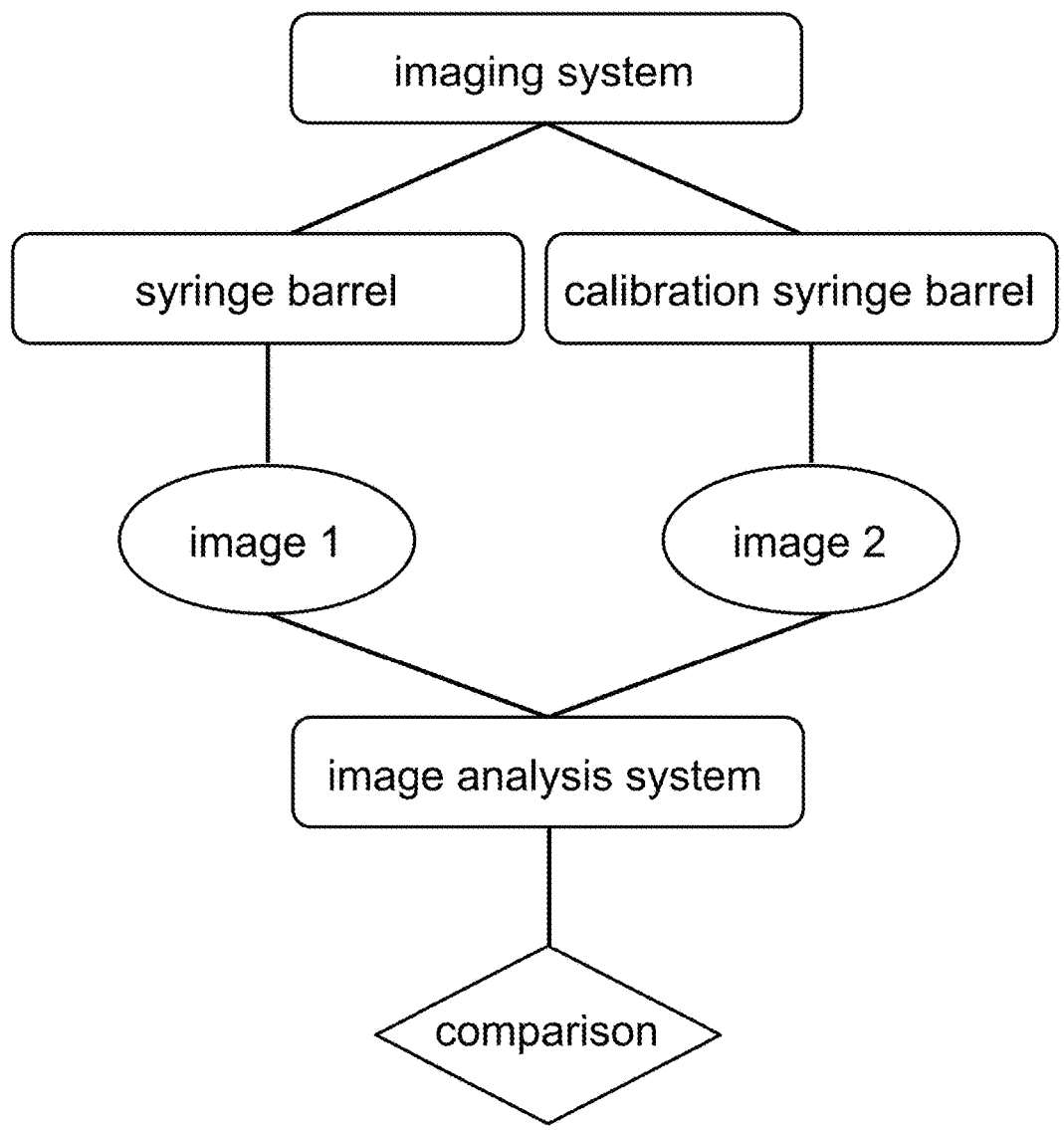
FIG. 1 shows a flow chart of the method and system according to an exemplary embodiment of the invention.

Medical syringe barrels having the inner surface coated with cured silicone oil are used for calibration and detection of silicone oil in medical syringe barrels. For this purpose a curable Polydimethylsiloxane (PDMS) was used. For testing purposes the inventors subjected the curable PDMS to a variety of conditions to create samples with a number of different dewetting properties with respect to the aqueous solution in the syringe barrel (Table 1).

| Test # | Storage Conditions |
|---|---|
| 1 | Stored at room temperature for 2 days |
| 2 | Incubated at 44° C. for 2 days |
| 3 | Placed in furnace at 120° C. for 1 hour then stored at room temperature for 2 days |
| 4 | Placed in cold store at 2-8° C. for 2 days |
| 5 | Filled with cell-grade water and placed in cold store at 2-8° C. for 2 days. |
| 6 | Immediately placed in freezer and stored for 2 days |
| 7 | Filled with cell grade water and stored at room temperature for two days |
| 8 | Sprayed with nozzle temperature of 75° C. and then stored for two days at room temperature |
| 9 | Sprayed with nozzle temperature of 75° C. and sample heated with heat gun and then stored for two days at room temperature |

In one example a modified PDMS oil (Sylgard 184, DowHCorning) was used. Sylgard 184 is a vinyl terminated PDMS oil, which when mixed with the appropriate curing agent (e.g. Dimethyl, methylhydrogen siloxane copolymer) becomes a clear solid with transparent optical properties identical to that of the unmodified PDMS oil. For details regarding Sylgard 184 please visit the website at http://www.dowcorning.com/applications/search/default.aspx?R=131EN or http://www.dowcorning.com and search for Sylgard 184.

The method for producing these samples uses an IVEK spray system to distribute 0.2 µL of the oil (which had already been mixed with the appropriate curing agent) into a typical syringe barrel (OMPI, 1 mL Long Standard). The samples were exposed to a variety of external conditions after spraying to observe the effects of the dewetting process on the silicone oil layer, as well as to create silicone oil layers with different morphological properties.

The results represent a proof of concept for the use of a curable PDMS solution to develop high quality calibration samples. The method of spraying allows for the creation of calibration samples for any type of pharmaceutical container chosen by a client. This allows the samples not only to be used for calibration when setting up/testing machines, but also to be used for daily checks in industrial settings, such as required by the stringent process controls currently in place in the pharmaceutical industry.

Appendix A in U.S. Provisional Application 62/242,346 filed Oct. 16, 2015 shows heat maps obtained by a ZebraSci Flex System. Heat maps are used throughout the pharmaceutical industry to detect the presence of silicone oil inside a vial, as well as to quantify the distribution of the oil throughout the vial. Appendix B in U.S. Provisional Application 62/242,346 filed Oct. 16, 2015 contains resulting patterns that resulted from varying storage conditions.

Figure 2A:
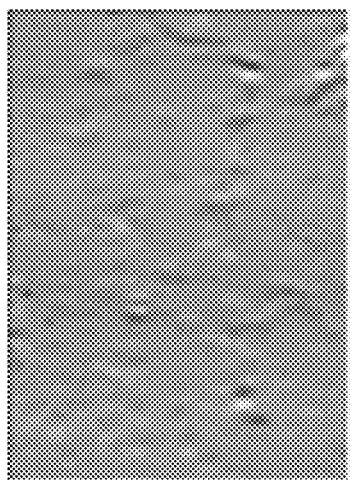
FIGS. 2A-B show according to an exemplary embodiment of the invention images obtained using the ZebraSci imaging system (ZebraSci, Inc. Temacula, Calif.) showing the stability of silicone oil distribution after two fillings with water.
Figure 2B:
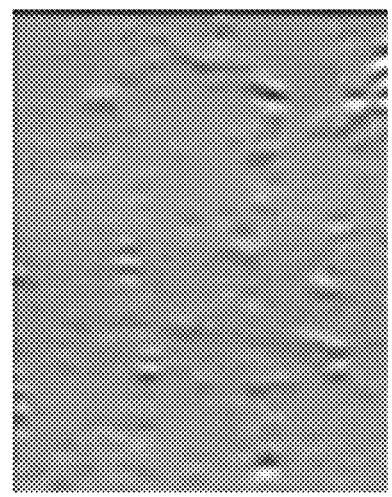

FIG. 2 shows the stability of the silicone oil layer after curing. Using samples from a test performed by the inventors, a sample was imaged and filled with water 2 times, emptied and then imaged again. The before and after images clearly show that the silicone oil layer is stable, a feature that uncross linked silicone oil materials lack.

Figure 3:
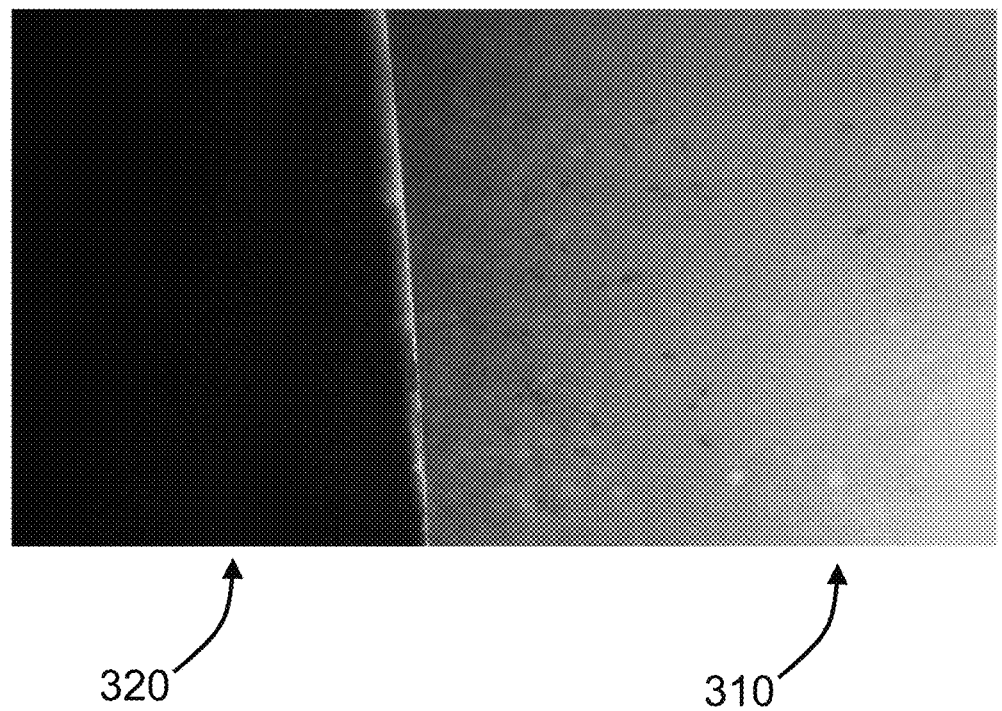
FIG. 3 shows according to an exemplary embodiment of the invention an image obtained using fluorescence microscopy clearly showing the areas covered with silicone oil on a glass microscope slide, which are indicated by 310.

The mixture used in the examples is Polydimethylsiloxane (PDMS), which under normal conditions does not fluoresce, and also is difficult to image when utilizing standard lighting and microscopy techniques. Different doping agents could be added to the mixture so as to make it visible under a fluorescing microscope. In one example, the resulting mixture could be doped with small amounts of additional chemicals to enhance the ability to detect the presence of the stabilized silicone oil layer. A Fluorescent tag can be mixed with the silicone oil so that fluorescence microscopy techniques can be utilized for high resolution mapping of the presence of silicone oil with in the vial. FIG. 3 shows an image where the Bodipy 493/503 (ThermoFisher Scientific, 4,4-Difluoro-1,3,5,7,8-Pentamethyl-4-Bora-3a, 4a-Diaza-s-Indacene) was added to allow for detection of the silicone oil using fluorescence microscopy. The dark area 320 in the image in FIG. 3 is an area of a glass slide with no silicone oil, and the bright 'green' 310 area represents the presence of the oil. It should be noted that while Bodipy 493/503 was utilized in this experiment a number of other fluorescent tags could have been used (fluorophore, Nile Red, Quantum dots, etc.).

In another example, vinyl-terminated PDMS from Dow Corning (Sylgard 184) was used. 10 mL of this mixture was mixed under heat with a fluorescing agent and after removal of any applicable mutual solvent a curing agent was mixed into the solution using a 10:1 ratio. This allowed for the creation of not just a PDMS mixture that would fluoresce under specific conditions, but also could be cured onto the surface of a sample to prevent it from moving.

Figure 4:
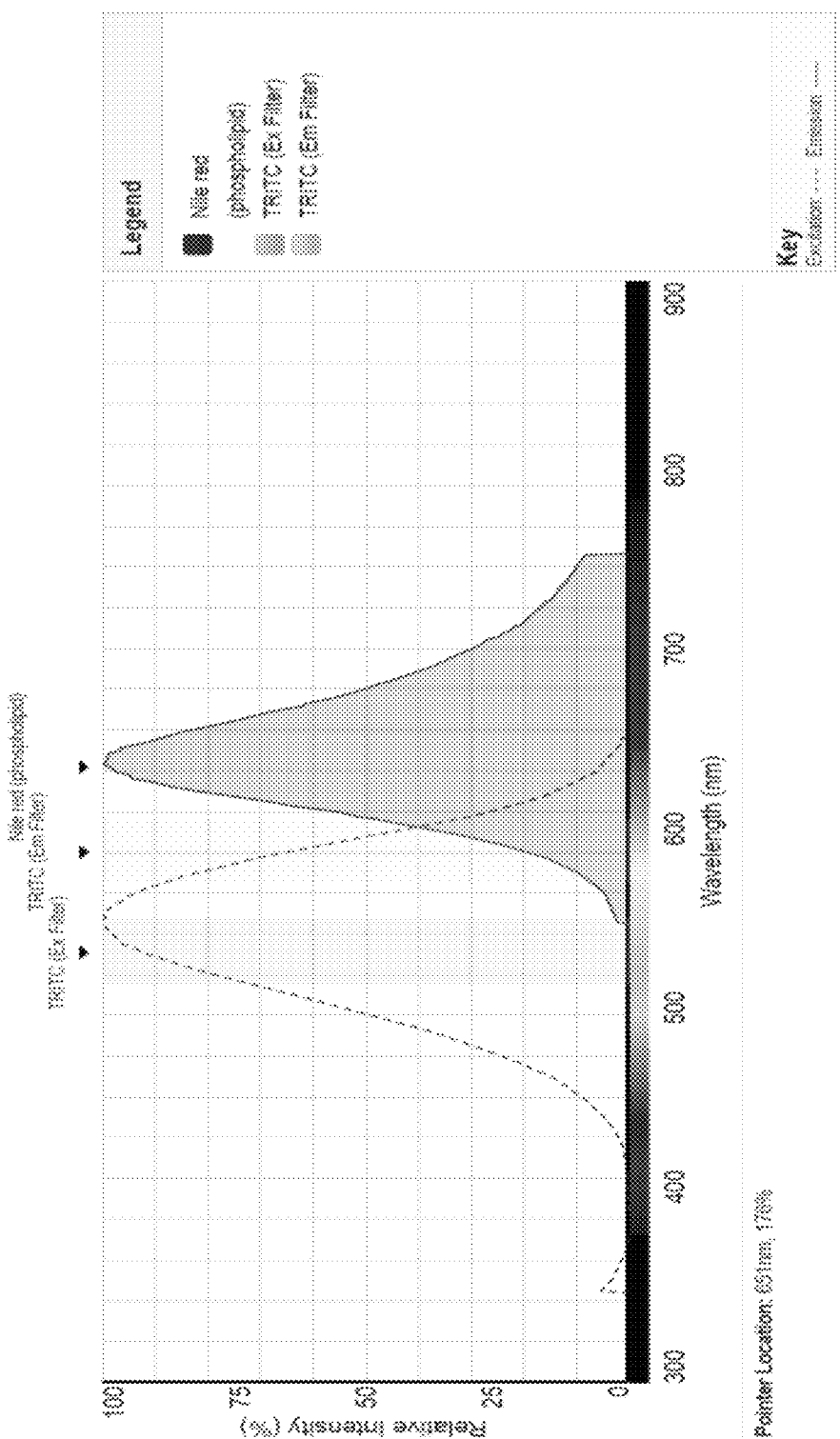
FIG. 4 shows according to an exemplary embodiment of the invention the excitation energy at different wavelengths based on the fluorescent agent as well as highlighting the filtered areas used in this experiment.
Figure 5:
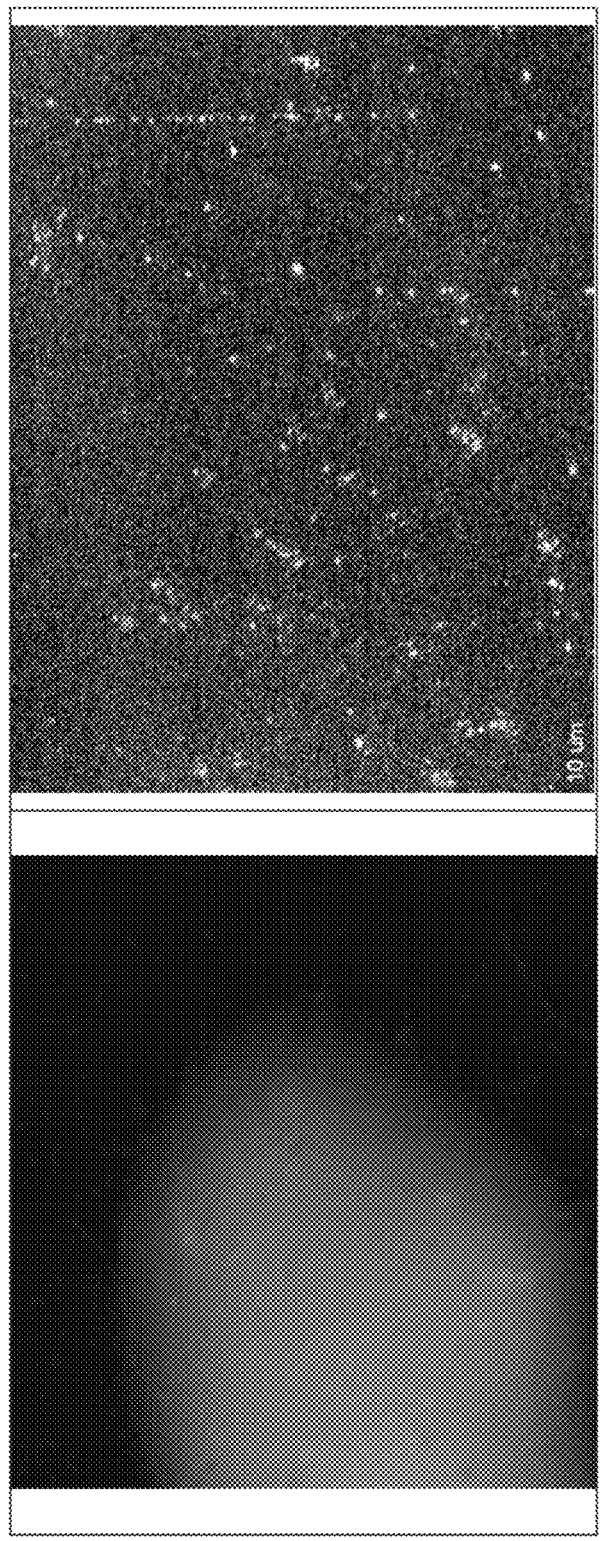
FIGS. 5A-B show according to an exemplary embodiment of the invention (FIG. 5A) grey-scale image showing Nile red dispersion throughout silicone oil. The black area (510) represents the area uncovered with silicone oil. The grey areas (520) show silicone oil with nile red distributed throughout the oil.

In one experiment we utilized a Nile Red (obtained from Sigma-Aldrich, CAS Number 7385-67-3) doping agent in the Sylgard mixture. Nile red is a phospholid agent FIG. 4 shows an example showing the emission, excitation as well as the results of TRITC filtering on the wavelengths when Nile Red is used. The results are shown in FIG. 5.

Figure 6:
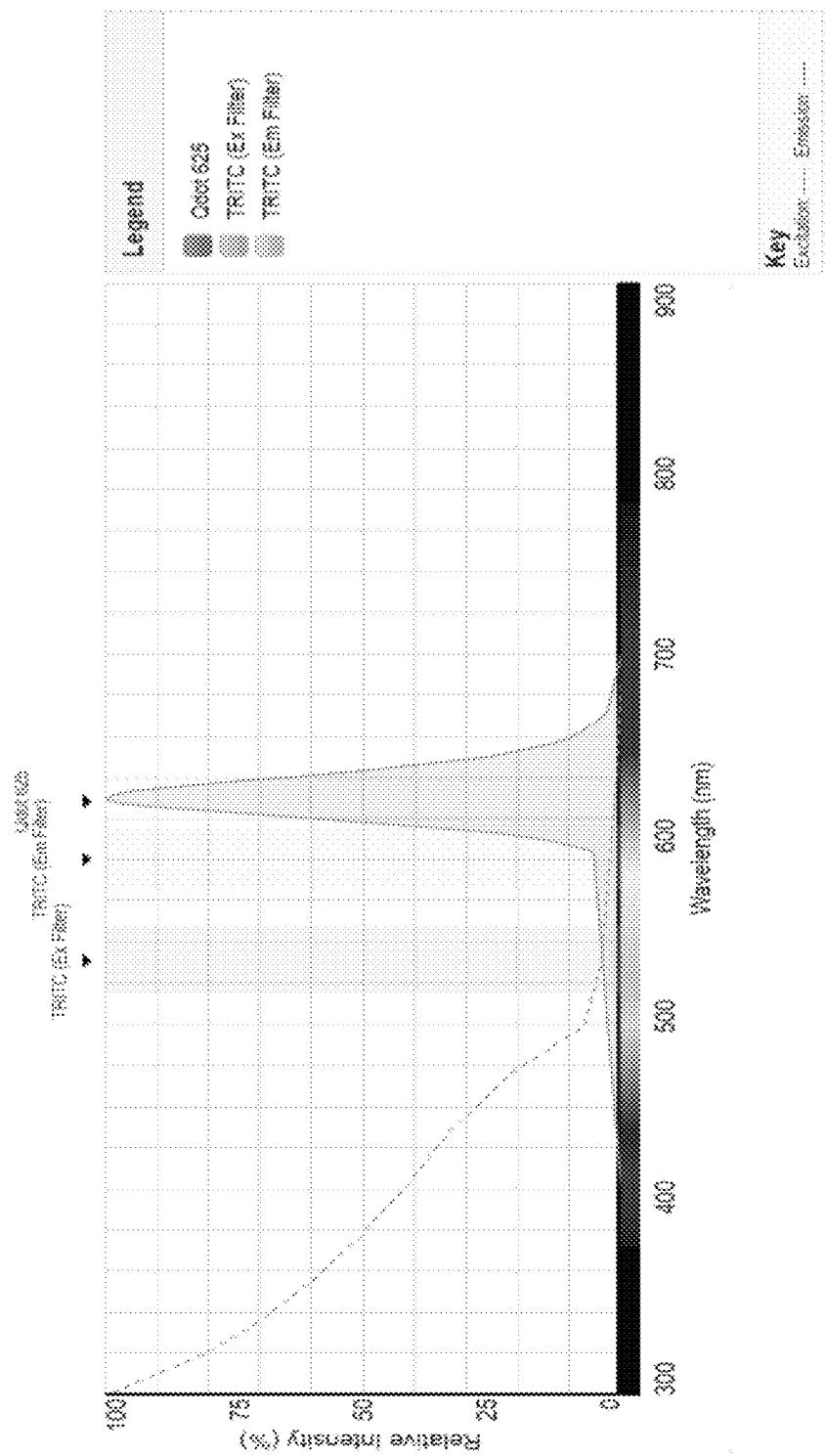
FIG. 6 shows according to an exemplary embodiment of the invention the excitation energy at different wavelengths based on the fluorescent agent as well as highlighting the filtered areas used in this experiment.
Figures 7A, 7B:
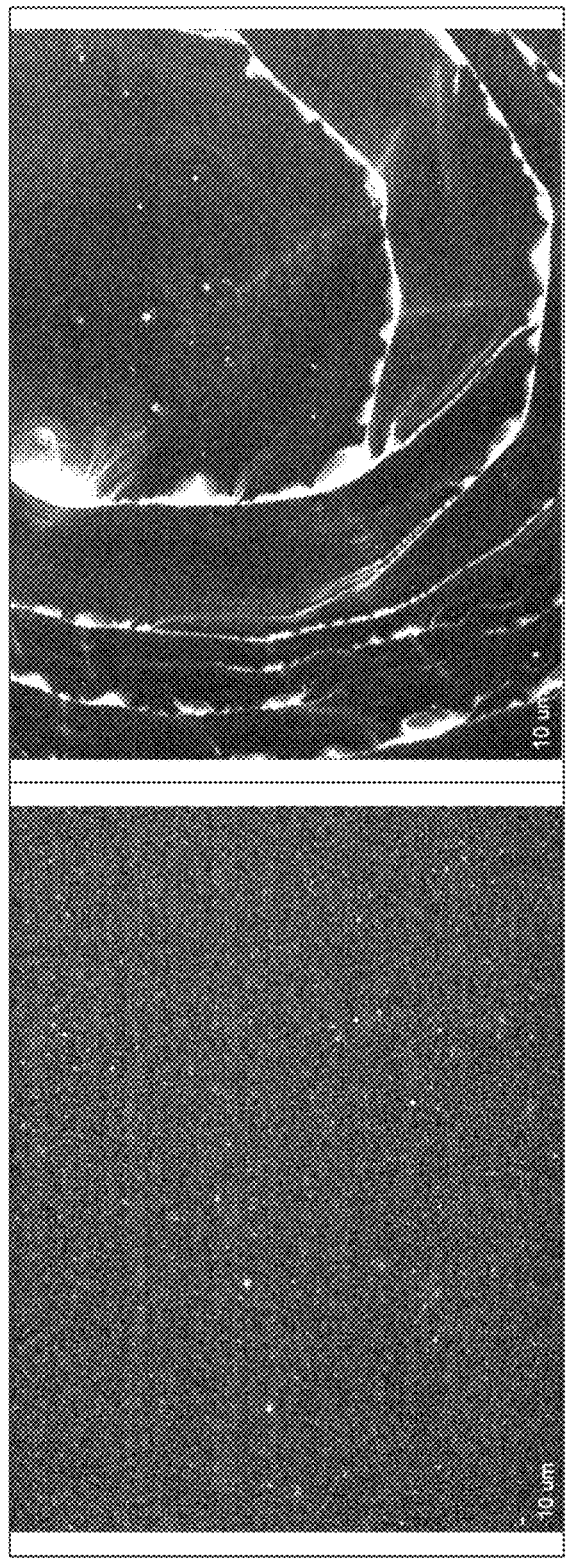
FIGS. 7A-B show according to an exemplary embodiment of the invention.
Figure 9:
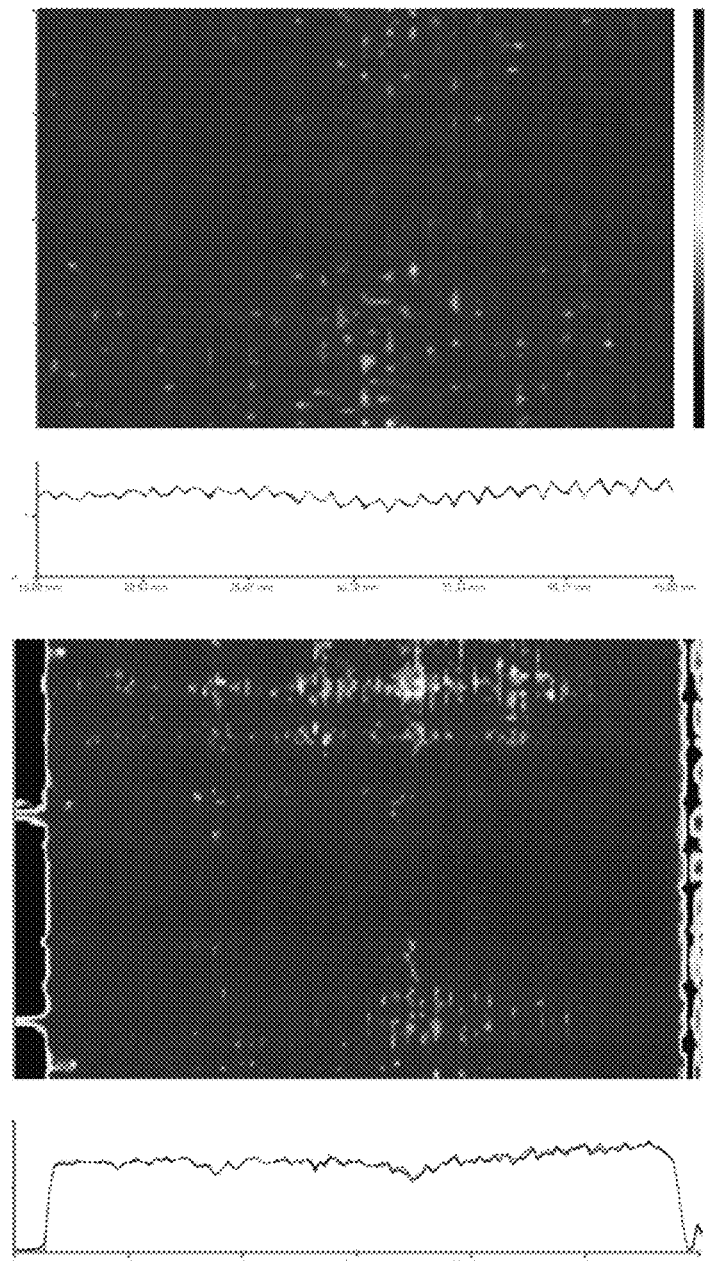
Figure 11:
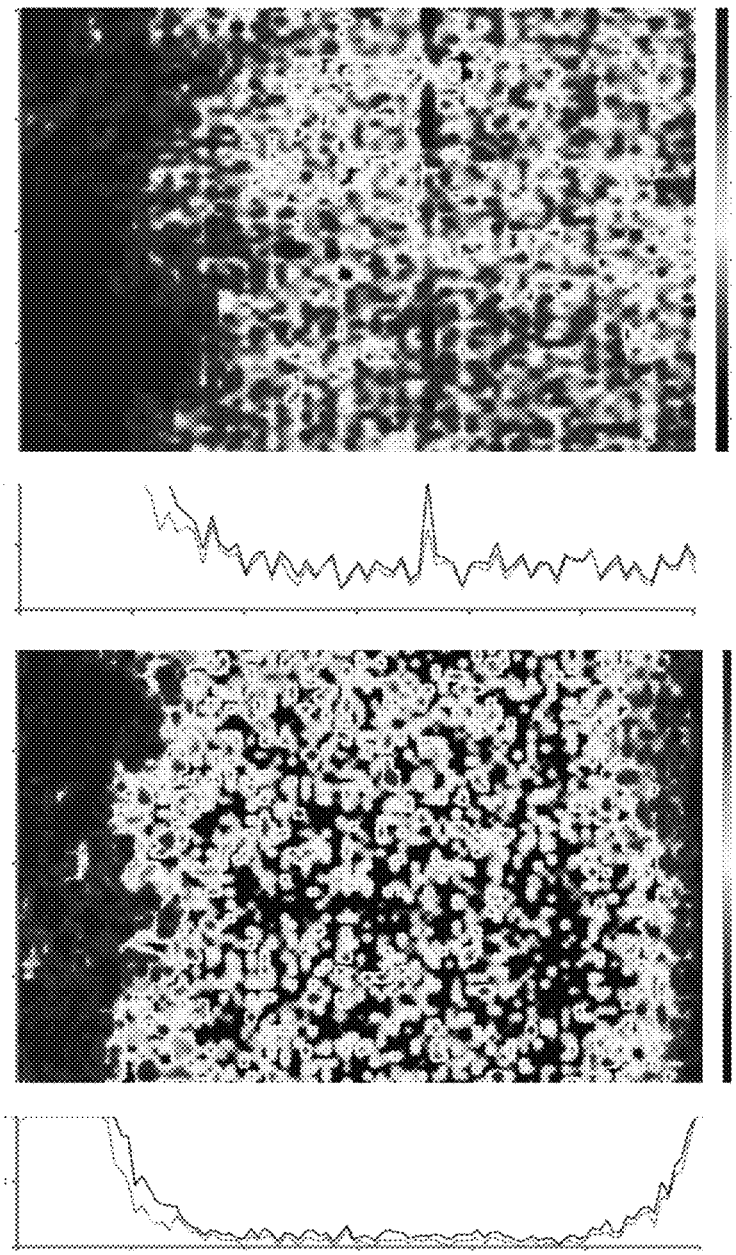
Figure 12:
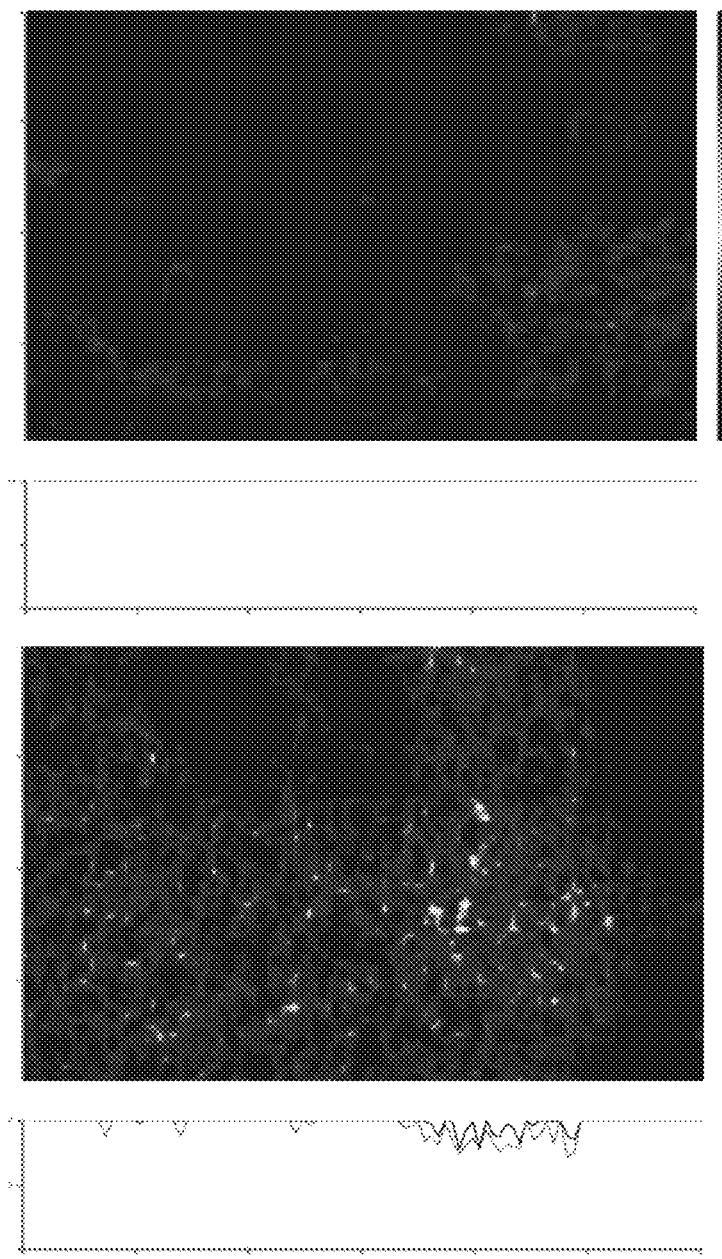

In another experiment, Sylgard 184 was doped using quantum dots. FIG. 6 shows an image giving the same emission and excitation information as for the Nile red experiment (FIG. 4). The mixture was created using a mutual Toluene solvent that was removed using low heat before adding the curing agent. The results are shown in FIG. 7.

What is claimed is:

1. A method of calibration and detection of silicone oil in syringe barrels, comprising:
   (a) providing a syringe barrel which has the inner surface coated with a silicone oil;
   (b) obtaining an image with an imaging system of the inner surface of the syringe barrel coated with the silicone oil, wherein the imaging system is capable of detecting silicone oil;
   (c) determining with a computer image analysis program executed by a computer a distribution pattern of the silicone oil at the inner surface from the obtained image;
   (d) determining by the computer image analysis program executed by the computer a comparison between (i) the distribution pattern of the silicone oil at the inner surface of the syringe barrel, with (ii) a calibration distribution pattern of an inner surface of a calibration syringe barrel coated with a cured silicone oil, wherein the silicone oil in the cured silicone oil is the same silicone oil as in the syringe barrel, wherein the calibration distribution pattern of the cured silicone oil is obtained from a calibration image obtained with the imaging system of the inner surface of calibration syringe barrel; and
   (e) outputting the comparison by the computer image analysis program executed by the computer.

2. The method as set forth in claim 1, wherein the cured silicone oil is chemically doped with a fluorescent material or a fluorescent tag that can be dissolved in silicone oil.

3. The method as set forth in claim 1, wherein the cured silicone oil is chemically or physically doped with a hydrophobic quantum dot.

4. The method as set forth in claim 1, wherein the cured silicone oil is a curable Polydimethylsiloxane (PDMS).

5. The method as set forth in claim 1, wherein the outputting the comparison comprises heatmaps.

6. A system for calibration and detection of silicone oil in syringe barrels, comprising:
   (a) a syringe barrel which has the inner surface coated with a silicone oil;
   (b) an imaging system capable of obtaining an image and detecting silicone oil of the inner surface of the syringe barrel;
   (c) a computer image analysis program executed by a computer to analyze a distribution pattern of the silicone oil at the inner surface from the obtained image;
   (d) the computer image analysis program executed by a computer capable of determining a comparison between (i) the distribution pattern of the silicone oil at the inner surface of the syringe barrel, with (ii) a calibration distribution pattern of an inner surface of a calibration syringe barrel coated with a cured silicone oil, wherein the silicone oil in the cured silicone oil is the same silicone oil as in the syringe barrel, wherein the calibration distribution pattern of the cured silicone oil is obtained from a calibration image obtained with the imaging system of the inner surface of calibration syringe barrel; and
   (e) the computer image analysis program executed by a computer capable of outputting the comparison.

7. The system as set forth in claim 6, wherein the cured silicone oil is chemically doped with a fluorescent material or a fluorescent tag that can be dissolved in silicone oil.

8. The system as set forth in claim 6, wherein the cured silicone oil is chemically or physically doped with a hydrophobic quantum dot.

9. The system as set forth in claim 6, wherein the cured silicone oil is a curable Polydimethylsiloxane (PDMS).

10. The system as set forth in claim 6, wherein the outputting the comparison comprises heatmaps.

11. A calibration syringe barrel, comprising: a syringe barrel wherein the inner surface of the syringe barrel is coated with a cured silicone oil, wherein the cured silicone oil defines a reference silicone oil distribution pattern, wherein the reference silicone oil distribution pattern is useful as a reference pattern for a silicone oil distribution pattern of other syringe barrels which have the inner surface coated with silicone oil, and wherein the silicone oil in the cured silicone oil is the same silicone oil as in the other syringe barrels.

* * * * *